United States Patent [19]

Geerts

[11] Patent Number: 5,480,848
[45] Date of Patent: Jan. 2, 1996

[54] CATALYST COMPOSITION AND THE USE IN OLEFIN POLYMERIZATION

[75] Inventor: Rolf L. Geerts, Bartlesville, Okla.

[73] Assignee: Phillips Petroleum Company, Bartlesville, Okla.

[21] Appl. No.: 236,810

[22] Filed: May 2, 1994

Related U.S. Application Data

[62] Division of Ser. No. 80,899, Jun. 22, 1993, Pat. No. 5,354,721.

[51] Int. Cl.$^6$ .................................................. C08F 4/42
[52] U.S. Cl. ......................... 502/103; 502/107; 502/152; 502/153; 502/155; 526/133
[58] Field of Search .................................. 502/103, 107, 502/152, 153, 155; 526/133

[56] References Cited

U.S. PATENT DOCUMENTS

| | | | |
|---|---|---|---|
| 4,496,699 | 1/1985 | Rekers et al. | 526/105 |
| 4,952,714 | 8/1990 | Welborn et al. | 556/179 |
| 5,091,352 | 2/1992 | Kioka et al. | 502/103 |
| 5,354,721 | 10/1994 | Greets | 502/117 |

FOREIGN PATENT DOCUMENTS

| | | |
|---|---|---|
| 348126 | 6/1989 | European Pat. Off. . |
| 4203753 | 8/1993 | Germany . |

*Primary Examiner*—Asok Pal
*Attorney, Agent, or Firm*—Edward L. Bowman

[57] ABSTRACT

A catalyst system comprising a transition metal-containing polymerization catalyst and a solid organoaluminoxy product produced by contacting a solution of an organoaluminoxane with an organic borane compound which is free of acidic hydrogen. The use of the catalyst system for the polymerization of olefins is also included.

26 Claims, 1 Drawing Sheet

CATALYST COMPOSITION AND THE USE IN OLEFIN POLYMERIZATION

This application is a Division of application Ser. No. 08/080,899, now U.S. Pat. No. 5,354,721.

The present invention relates to aluminoxy products. The term organo-aluminoxy as used herein refers to organic compounds having a plurality of aluminum atoms each bound to at least two oxygen atoms. In another aspect, the present invention relates to a method of modifying organic aluminoxanes to make them suitable for use in particle form polymerization. In still another aspect, the present invention relates to a metallocene catalyst comprising a modified organic aluminoxane. In still another aspect, the present invention relates to a process for polymerizing olefins using the modified organic aluminoxane.

BACKGROUND OF THE INVENTION

Organic aluminoxanes are one form of aluminoxy compound. Organic aluminoxanes can be produced by the partial hydrolysis of hydrocarbyl aluminum compounds. Such aluminoxanes have been found useful in a variety of chemical reactions, including utility as catalyst components for polymerization catalysts, especially in high activity metallocene catalyst systems.

The combination of such aluminoxanes with metallocenes has been shown to be useful for certain types of olefin polymerization. One of the earliest patents containing such a disclosure is U.S. Pat. No. 3,242,099, the disclosure of which is incorporated herein by reference. Such metallocene catalysts have been used in homogeneous solution polymerization. Since such homogeneous catalyst systems are soluble in the polymerization medium it is generally observed that the resulting polymer has low bulk density.

Further, attempts to use metallocene/aluminoxane catalysts in a slurry or particle form type polymerization have not heretofore been found to be commercially feasible. In slurry or particle form polymerization, the polymerization conditions are selected such that the polymer forms as discrete particles which are insoluble in the polymerization reaction medium during the polymerization. It has been observed that when such particle form polymerizations are carried out in the presence of a metallocene/aluminoxane catalyst system, large amounts of polymeric material are formed on the surfaces of the polymerization vessel. This fouling is particularly detrimental in a particle form process since it produces an adverse effect on the heat transfer and also results in the need for periodic if not continuous cleaning of the reactor. In order to have a metallocene/aluminoxane catalyst useful in a commercial continuous particle form process such as those using a loop reactor, it is necessary to have a catalyst system which will not cause significant amounts of reactor fouling.

It is known that a solid form of aluminoxane can be obtained by treating a commercial organo aluminoxane solution with a countersolvent; however, even that solid has been found to cause reactor fouling in slurry polymerizations. Even when a countersolvent is used to precipitate the aluminoxane onto an insoluble particulate carrier reactor fouling is still a problem in slurry, i.e. particle form polymerization.

An object of the present invention is to provide a new organo-aluminoxy composition which while still active as a cocatalyst for a transition metal polymerization catalyst, at the same time does not produce significant reactor fouling in a particle form process.

Another aspect of the present invention relates to a method for making this new organo-aluminoxy composition.

Still another aspect of the present invention relates to polymerization catalyst systems comprising a transition metal compound and the new organo-aluminoxy composition.

Still yet another aspect is to provide a solid organo-aluminoxy composition having a surface area greater than that of the solid resulting from the vacuum stripping of an aluminoxane solution. Inventive solids having a surface area as high as 300 m²/g as determined by a BET test have been prepared.

Another object is to provide a stable solid metallocene polymerization catalyst comprising the combination of a metallocene and the inventive solid aluminoxane.

Still yet another aspect of the present invention relates to the polymerization of olefins using the new organo-aluminoxy composition as the cocatalyst, especially in particle form polymerizations.

Other aspects, objects and advantages of the present invention will become apparent to those skilled in the art having the benefit of the following disclosure.

SUMMARY OF THE INVENTION

Figure 1:
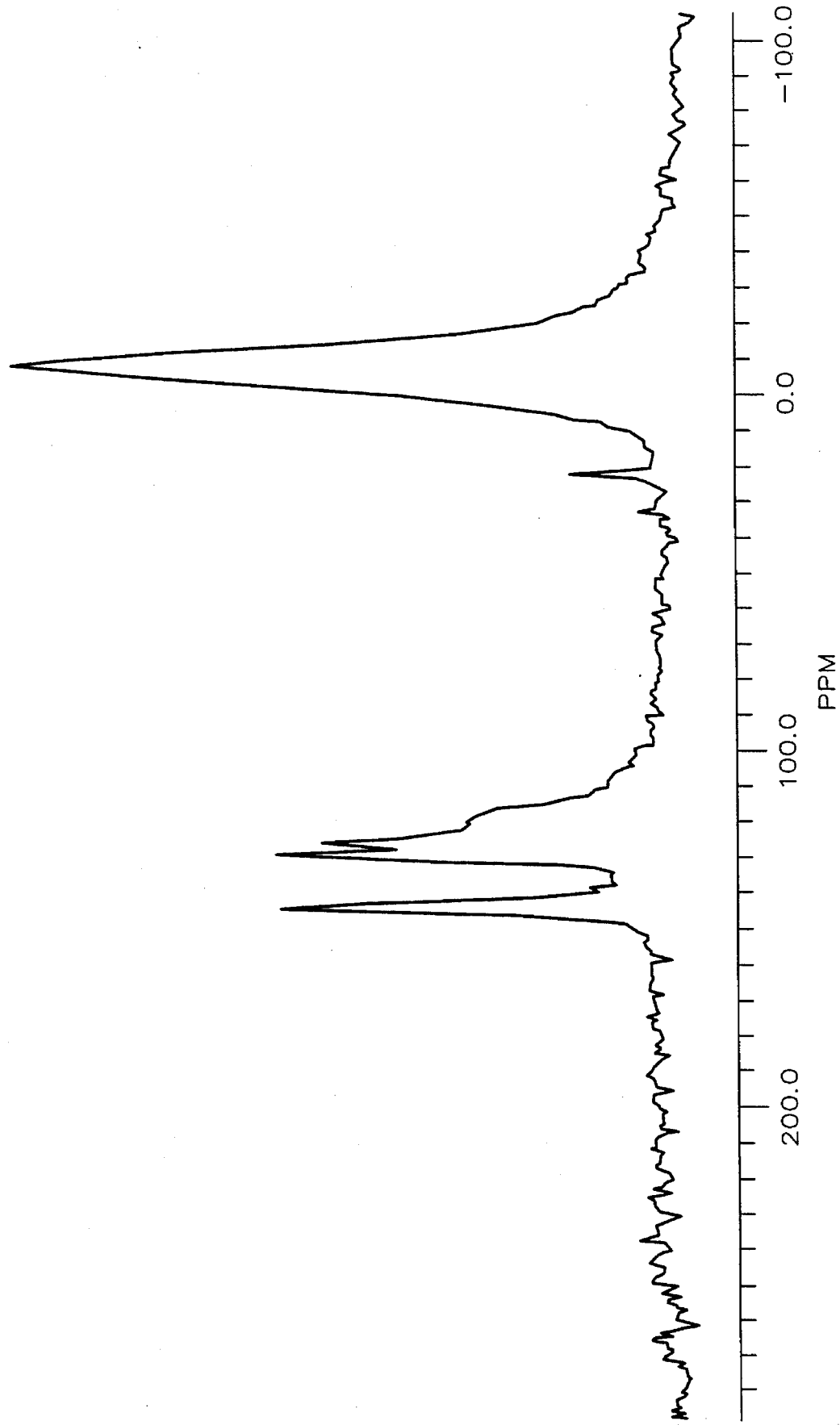
FIG. 1 is a graph showing a $^{13}$C-NMR spectra of the solid resulting from the reaction of a commercial methylaluminoxane with catechol borane.

In accordance with the present invention, a solid organo-aluminoxy product is produced by reacting an organic aluminoxane with an acidic hydrogen free organic borane compound containing

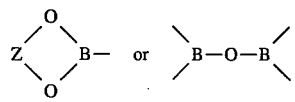

functionality. (The term "acidic hydrogen free" as used herein is intended to refer to borane compounds free of functionality having active acidic hydrogen, e.g. hydroxy hydrogens, acid hydrogens, and phenolic hydrogens.)

In accordance with another aspect of the present invention, a catalyst system suitable for the polymerization of olefins is produced by combining the new organo-aluminoxy composition with a transition metal based olefin polymerization catalyst.

Still another object of the present invention is to provide a relatively stable solid olefin polymerization catalyst comprising a metallocene and the inventive solid aluminoxy composition.

In accordance with still another aspect of the present invention, there is provided a process for producing polyolefins comprising contacting at least one olefin under suitable conditions with a catalyst system comprising a suitable catalyst and the inventive organo-aluminoxy composition. In accordance with still another aspect of the present invention, there is provided a new organo-aluminoxy composition resulting from the reaction of the aluminoxane with the borane compound.

DETAILED DESCRIPTION OF THE INVENTION

In accordance with the present invention, organic aluminoxanes are modified to produce a new solid organo-aluminoxy composition that can be used as a cocatalyst in olefin polymerization.

Various techniques are known for making organic aluminoxanes. One technique involves the controlled addition of water to a trialkylaluminum. Another technique involves combining a trialkylaluminum and a hydrocarbon with a compound containing water of adsorption or a salt containing water of crystallization. The present invention is considered applicable to any of the commercially available organic aluminoxanes that are soluble in a hydrocarbon.

The exact structure of organic aluminoxanes is often the subject of much discussion between scholars. It is generally accepted that the aluminoxanes are oligomeric, linear and/or cyclic hydrocarbyl aluminoxanes having repeating units of the formula

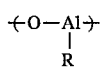

Typically the linear aluminoxanes are said to contain oligomers of the formula:

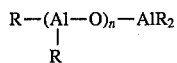

The oligomeric, cyclic aluminoxanes are generally viewed as having the formula:

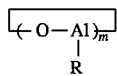

In the above formulas, R is a hydrocarbyl group, typically a $C_1$–$C_8$ alkyl group, and n is typically 2 to 50, preferably 4 to 40, m is typically 3 to 50, preferably 4 to 40. Generally, the aluminoxanes are more active as polymerization catalysts when m and n are greater than 4, more preferably at least about 10. Typically in the aluminoxanes used in the polymerization of olefins R is predominantly methyl or ethyl. Preferably at least about 30 mole percent of the repeating groups have an R which is methyl, more preferably at least 50 mole percent, and still more preferably at least 70 mole percent of the repeating units have methyl as the R group.

Some experts believe that the resulting oligomeric aluminoxane products have some significant amounts of unreacted yet somehow strongly bonded trialkylaluminums associated therewith. Among some researchers there has even been the theory that perhaps the trialkylaluminums associated with the aluminoxane is actually the material which causes the aluminoxane to be effective as a cocatalyst with metallocenes and other transition metal olefin polymerization catalysts. See L. Resconi et al, *Macromolecules*, 1990 (23), 4489–4491.

It is considered that the present invention can be applied to any of the above discussed aluminoxanes. Aluminoxanes are generally obtained commercially in the form of hydrocarbon solutions, generally aromatic hydrocarbon solutions, since the more active higher molecular weight aluminoxanes are generally insoluble in aliphatic hydrocarbons. Unless these samples have been subjected to special treatment, they typically contain trialkylaluminum as well as the oligomeric aluminoxane. The trialkyl aluminums generally include those in which the alkyl groups contain 1 to 8 carbon atoms, most generally one to two carbon atoms.

The present invention is particularly useful for modifying aluminoxane solutions containing both trialkylaluminums and aluminoxanes, particularly the aluminoxanes wherein n of the above formula is at least about 2 and m is at least about 3, and even more preferably wherein are both greater than 4. The preferred aluminoxanes for use in the present invention are those in which R of the above formulas is methyl or ethyl, preferably methyl.

The inventive method for producing the solid organoaluminoxy composition comprises contacting a solution of an organo aluminoxane with a suitable amount of an acidic hydrogen free organic borane compound containing

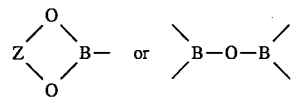

functionality under suitable conditions, wherein Z is a bridging unit between the two oxygen atoms.

Examples of such compounds include compounds of the formula

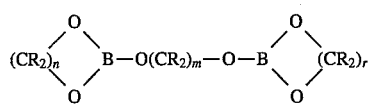

and

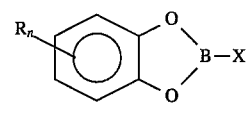

and

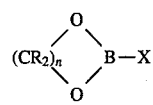

and

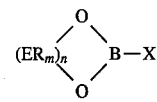

and $R_2BOBR_2$ wherein each R is individually selected from hydrogen and hydrocarbyl radicals, preferably aryl or alkyl radicals having 1 to 20 carbon atoms; n, m, and r are integers preferably in the range of 1 to 10; each E is individually selected from C, Si, Ge, Sn, B, Ga, In, P, As, and Sb with the proviso that at least one E is not C; and X is selected from hydrogen, hydrocarbyl radicals having 1 to 20 carbon atoms, halides, hydrocarbyloxy radicals having 1 to 20 carbon atoms, and $-NR_2$ radicals. Some specific examples include catechol borane, diphenyl borinic anhydride, dibutyl borinic anhydride, trimethylene borate, methyl catechol borane and the like.

The reaction of the borane with the aluminoxane can be carried out in any suitable manner. One particularly desirable technique simply involves contacting the two reactants in a suitable liquid diluent. One preferred technique involves contacting a hydrocarbon solution of the aluminoxane with a hydrocarbon solution of the borane compound. Another technique involves contacting a hydrocarbon solution of the aluminoxane with a countersolvent to produce a slurry comprising soluble aluminoxane and insoluble particulate aluminoxane and then contacting the resulting slurry with a solution of the borane compound. It is also within the scope of the present invention to carry out the reaction of the borane compound and the aluminoxane in the presence of a particulate diluent so that the insoluble product becomes deposited upon the particulate diluent. Typical particulate diluents would include such inorganic materials as silica, alumina, aluminum phosphate, silica-alumina, titania, kaolin, fumed silica, and the like.

It is also within the scope of the present invention to prepare the inventive particulate organo-aluminoxy composition and then combine it with a solution of a trialkylaluminum compound, i.e. trimethylaluminum or others of the type mentioned above, and then to contact the resulting slurry with additional mounts of the borane compound. It is believed that this process may provide a method for further increasing the molecular weight of the particulate aluminoxy composition that is initially produced by reacting the aluminoxane with the borane compound. Obviously, such a process could be repeated several times to obtain the desired level of molecular weight, particle size, bulk density, or other characteristic that is desired for a particular application.

The amount of the borane compound employed relative to the aluminoxane can vary over a wide range depending upon the particular results desired. A technique which has been used in this invention for reflecting the ratio of the borane to the aluminoxane, involves the use of a calculated amount for the amount of aluminoxy aluminum in the aluminoxane solution. As used herein the term "calculated aluminum" is the value obtained by using a vacuum to strip the solvent off a known volume of the aluminoxane solution, weighing the recovered solid, and dividing the weight of the solid per milliliter by the average molecular weight of the aluminoxy units, (i.e. 58 for methylaluminoxane), so that one obtains a calculated value for the number of moles of aluminum per volume of the aluminoxane solution that is to be reacted with the borane compound. It is theorized that a substantial portion of any free trihydrocarbylaluminum in the aluminoxane solution is removed when the solvent is stripped off. Any trihydrocarbylaluminum that is present in the solid recovered after vacuum stripping, is not considered to have a significant effect upon the calculated aluminum value. Using this method, the atomic ratio of the boron in the borne compound to the calculated aluminum in the aluminoxy units of the aluminoxane employed will generally be in the range of about 1/20 to about 1/3, more preferably about 1/15 to about 1/5, still more preferably about 1/7.

As noted above, the commercial aluminoxane solutions, generally contain at least some trihydrocarbylaluminum, in addition to aluminoxy units. Generally the trihydrocarbylaluminum accounts for about 0.1 to about 35 wt. percent of the aluminum in the solution. It is generally preferred for the borane compound to be employed in such an amount that the molar ratio of the borane compound to the trihydrocarbylaluminum will be at least about 0.3334/1.

In view of the demonstrated activity of the borane precipitated organo aluminoxy products of the present invention, it is considered that such solid organo aluminoxy products will be suitable as replacements for soluble aluminoxy products in polymerization reactions. Accordingly, the inventive solid aluminoxanes should be suitable as catalyst components with any number of the transition metal-containing olefin polymerization catalysts that have in the past been employed with soluble aluminoxanes. Some examples of such transition metal-containing catalysts are disclosed in the previously mentioned U.S. Pat. No. 3,242,099, the disclosure of which is incorporated herein by reference. The use of more than one such catalyst is also within the scope of the present invention. In a preferred embodiment, the catalyst portion of the catalyst system is selected from transition metal compounds of metals of Groups IVB, VB, and VIB. Examples of the transition metals thus include zirconium, titanium, hafnium, and vanadium. Such compounds can be represented by the formula $MX_n$ wherein M represents the transition metal atom and X represents a halogen atom or an organo group, and n is the valence state of the transition metal. Some illustrative examples of such transition metal compounds include vanadium dichloride, vanadium trichloride, vanadium tetrachloride, vanadium pentafluoride, vanadium triiodide, titanium dibromide, titanium tetrachloride, titanium trichloride, titanium tetrafluoride, titanium tetraiodide, titanium tetrabromide, zirconium trichloride, zirconium tetrachloride, chromic chloride, titanium tetraethoxide, titanium tetrabutoxide, zirconium tetrabutoxide, dicyclopentadienyl titanium dichloride, dicyclopentadienyl zirconium dichloride, chromium (III) 2-ethylhexanoate, and the like.

In a particular preferred embodiment the transition metal catalyst component comprises a metallocene. Examples of metallocenes include compounds of the formula $ML_x$ wherein M is the transition metal, at least one L is a ligand coordinated to the transition metal compound having an alkyldienyl skeleton, the other L's can be selected from ligands having alkyldienyl skeletons, hydrocarbon radicals having 1 to 12 carbon atoms, alkoxy radicals having 1 to 12 carbon atoms, aryl oxy radicals having 6 to 12 carbon atoms, halogen, or hydrogen, and x is the valence of the transition metal. Other examples include the hetero-atom containing metallocenes such as disclosed in U.S. Pat. No. 5,057,475.

The term "alkyldienyl skeleton" is intended to include such ligands as cyclopentadienyl, alkyl-substituted cyclopentadienyl compounds such as methyl cyclopentadienyl, ethyl cyclopentadienyl, n-butyl cyclopentadienyl, dimethyl cyclopentadienyl, pentamethyl cyclopentadienyl, and the like. Other examples of such cycloalkyldienyl ligands include substituted and unsubstituted indenyls or fluorenyls, tetrahydroindenyls, and the like. Examples of such metallocenes are disclosed in U.S. Pat. No. 5,091,352, the disclosure of which is incorporated herein by reference. Some specific examples include bis cyclopentadienyl zirconium dichloride, bis(methylcyclopentadienyl) zirconium dichloride, and bis(n-butyl cyclopentadienyl) zirconium dichloride.

It is also within the scope of the present invention to have two of the L groups by cycloalkyldienyl-type groups which are bonded together by a suitable bridging group. Some such metallocenes are referred to herein as sandwich-bonded metallocenes. The term "sandwich-bonded metallocenes" is used herein to indicate that the metal of the metallocene is sandwiched between two opposed cycloalkyldienyl portions of the bridged ligand. Some examples of bridged sandwich bonded metallocenes include 1(9-fluorenyl)- 1-(cyclopentadienyl) methane zirconium dichloride, fluorenyl cyclopentadienyl dimethyl methane zirconium dichloride, 1,2-bis-indenyl ethane hafnium dichloride and the like. Metallocenes also include so-called "half-sandwich-bonded", i.e. those in which only one of two cycloalkyldienyl portions is bonded to the metal. An example would be (1-fluorenyl- 1-cyclopentadienyl methane) zirconium trichloride.

It is also within the scope of the present invention to employ the inventive solid aluminoxy product in combination with the third generation supported high activity transition metal containing olefin polymerization catalysts. Some examples of typical high activity solid transition metal containing olefin polymerization catalysts include those disclosed in U.S. Pat. Nos. 4,326,988 and 4,394,291, the disclosures of which are incorporated herein by reference.

It is also within the scope of the invention to prepare a prepolymerized solid catalyst composition by combining the transition metal component and the inventive solid aluminoxy composition and conducting prepolymerization of an olefin to produce an active prepolymerized solid which is later used in a polymerization zone.

The particular polymerization conditions employed using the inventive compositions can vary depending upon the particular results desired. It is considered that the inventive solid organo aluminoxy product can be employed in solution, suspension, and gas phase polymerization of a wide range of olefinically unsaturated monomers. The ratio of the transition metal catalyst to the inventive solid aluminoxy product can vary widely depending upon the particular catalyst selected and the results desired. Typically, the atomic ratio of aluminum in the inventive aluminoxy product to the transition metal is in the range of about 1/1 to about 5000/1, preferably about 15/1 to about 1000/1, and more preferably about 100/1 to about 1000/1. For a particular transition metal catalyst it is considered that polymerizations can be carried out under the same conditions as would be suitable for prior art aluminoxanes.

Examples of some monomers for polymerization include ethylene and alpha-olefins having 3 to 20 carbon atoms, such as propylene, 1-butene, 1-hexene, 4-methyl-1-pentene, 1-octene, 1-hexadecene, cyclopentene, norborene, styrene, 4-methyl styrene, vinyl cyclohexane, butadiene, and the like and mixtures thereof.

The present invention is particularly useful in slurry type polymerizations since it allows one to carry out such polymerizations more effectively than has heretofore been possible. A particularly preferred type of slurry polymerization involves the continuous loop reactor type polymerization wherein monomer, feed, catalyst, and diluent, if employed, are continuously added to the reactor as needed and polymer product is continuously or at least periodically removed. Generally in such processes, ethylene is polymerized in the presence of a suitable liquid diluent, a higher alpha-olefin comonomer, and optionally, hydrogen. The polymerization temperature can vary over the range which will allow for slurry polymerization. Often the slurry polymerization would be conducted at a temperature in the range of about 60° C. to about 100° C., although higher and lower temperature can be used. The employment of hydrogen in such a continuous loop polymerization using the inventive cocatalyst can in some cases provide very interesting effects, specifically, broad molecular weight distribution. Polyethylenes of broader molecular weight distribution are produced by introducing only enough hydrogen to produce the desired melt index without reducing the molecular weight distribution. This is particularly surprising in that in the past, metallocene polymerizations employing a single metallocene catalyst have generally given narrow molecular weight distribution products, for example products having a molecular weight distribution in which the ratio of the weight average molecular weight to the number average molecular weight is in the range of about 2 to 3. While such narrow molecular weight can be made using the inventive material, it is also possible, by using the correct conditions with the inventive solid aluminoxy product in a slurry polymerization, to produce polyethylene in which the ratio of the weight average molecular weight to the number average molecular weight is as high as 21 or more, depending upon the particular metallocene employed.

A further understanding of the present invention and its objects and advantages will be provided by referring to the following examples.

EXAMPLE I

The inventive solid aluminoxane was prepared from a toluene solution of methylaluminoxane obtained from Schering which was reported to contain about 10 wt. percent methylaluminoxane. The process involved slurrying 10 mL (0.0113 mole calculated aluminoxane) solution in 50 mL of hexane. While this mixture was stirred 0.135 g (0.00113 mole) of catechol borane was added dropwise. The solution fumed slightly as copious precipitates formed. The slurry was stirred for 3 more hours and collected on a filter and dried. 0.4 g of solid product were obtained.

The resulting solid aluminoxane was then used to prepare a metallocene catalyst system. The catalyst was prepared by slurrying 0.13 g of the solid aluminoxane in 30 mL of hexane and then 1 mL of a 3 mg/mL toluene solution of bis(cyclopentadienyl) zirconium dichloride was added. The mixture was stirred overnight. Then the solids were collected on a filter and dried.

The resulting solid metallocene catalyst system was then evaluated for activity in the polymerization of ethylene under particle the solid catalyst system at about 70° C. in 2 liters of isobutane in the presence of hydrogen in an autoclave reactor. The partial pressure of isobutane and hydrogen was 175 psi and the total pressure was about 341 psi. The polymerization was carried out for 1 hour and yielded 78.9 g of dry polymer. That is equivalent to an activity of 780 g of polymer per gram of catalyst system per hour. The term "catalyst system" as used herein refers to the combination of both the metallocene and the solid aluminoxane. The activity expressed in terms of zirconium would obviously be much higher.

EXAMPLE II

In this case, a methylaluminoxane obtained from Ethyl Corporation was evaluated. The commercial methylaluminoxane was a 1.7 molar toluene solution. To a 10 mL portion of the toluene solution of methylaluminoxane, i.e. 0.017 mole MAO, was added 50 mL of hexane at room temperature. The turbid solution became cloudy white. To this stirred slurry was then added dropwise a 2 mL toluene solution of catechol borane containing 0.255 g (0.002125 mole) of catechol borane. The cloudy white suspension rapidly became more viscous as additional solids formed. The addition of the catechol borane was carried out over a 15 minute period. Then the slurry was stirred for an additional hour. The resulting slurry was then filtered to collect the solids and dried in a dry box. 1.1 g of solid aluminoxane was obtained.

A portion of the resulting solid catechol borane/aluminoxane reaction product was subjected to NMR analysis. A copy of the $^{13}C$ NMR spectra is shown in FIG. 1. The carbon NMR spectrum of the inventive solid is quite different than the spectrum obtained from a solid resulting merely from the evaporation of the solvent from a commercial MAO. Such a commercial MAO solid generally has only one major peak. The peaks of FIG. 1 above 100 ppm reflect the presence of the catechol functionality in the solid product. This was also confirmed by further $^{13}C$ NMR analysis involving dipolar dephasing. Also seen is residual toluene. The solid aluminoxane was also subjected to $^{11}B$ NMR analysis. The spectra revealed the fact that the solid product does in fact contain significant amounts of boron. Similarly a $^{27}AL$ NMR analysis was conducted and not surprisingly revealed that the solid contained substantial amounts of aluminum.

The inventive solid aluminoxane prepared from the Ethyl commercial material was then used to prepare a polymerization catalyst system. In this case, 0.5 g of the solid aluminoxane was added to 30 mL of hexane and then 2 mL of a 3.5 mg/mL hexane solution of bis(n-butyl cyclopentadienyl) zirconium dichloride was added. The resulting essentially colorless slurry was stirred for 2 hours at room temperature in a dry box. Then the solids were collected on a filter and dried to a constant weight.

This catalyst was then evaluated for the particle form polymerization of ethylene. The amount of the solid catalyst system employed was 0.0224 g. Again the polymerization was conducted at about 70° C. in 2 liters of isobutane in an autoclave in the presence of hydrogen. The partial pressure of the isobutane and hydrogen was about 147 psi. The total pressure was about 341 psi. The polymerization was carried out for 1 hr. and yielded 69.7 g of dry polymer having a melt index of 10.1 and a high load melt index of 268. It was easy to clean up the reactor and the polymer had relatively large particle size.

Under similar conditions another 1 hr. polymerization was conducted using 0.0223 g of the solid aluminoxane metallocene catalyst system and yielded 95.5 g of solid polyethylene having a melt index of 1.22 and a high load melt index of 41.

That which is claimed is:

1. An olefin polymerization catalyst system comprising at least one transition metal-containing olefin polymerization catalyst and the solid alkylaluminoxy product produced by contacting a solution of an organoaluminoxane with a suitable amount of an acidic hydrogen free organic borane compound selected from those having the formulas

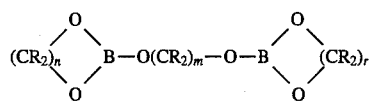

and

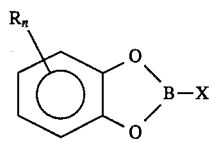

and

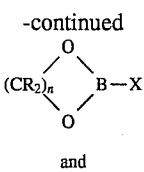

and

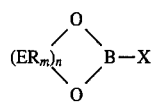

and $R_2BOBR_2$ wherein each R is individually selected from hydrogen and hydrocarbyl radicals, preferably aryl or alkyl radicals having 1 to 20 carbon atoms; n,m, and r are integers preferably in the range of 1 to 10; each E is individually selected from C, Si, Ge, Sn, B, Ga, In, P, As with the provisio that at least one E is not C, and Sb; and X is selected from hydrogen, hydrocarbyl radicals having 1 to 20 carbon atoms, halides, hydrocarbyloxy radicals having 1 to 20 carbon atoms, and —$NR_2$ radicals.

2. A catalyst system according to claim 1, wherein the solid alkylaluminoxy product was prepared by reacting catechol borane with methylaluminoxane and wherein at least one olefin polymerization catalyst is selected from metallocenes.

3. A catalyst system according to claim 2 wherein said metallocene is selected from the group consisting of bis(cyclopentadienyl) zirconium dichloride and bis(n-butyl cyclopentadienyl) zirconium dichloride.

4. A catalyst system according to claim 1 in which the combination of the solid alkyl aluminoxy product and the transition metal-containing olefin polymerization catalyst is a solid.

5. A process for producing polymer comprising contacting at least one olefin under suitable conditions with the catalyst system comprising at least a one transition metal-containing olefin polymerization catalyst and a solid organo-aluminoxy produced by contacting a solution of an organoaluminoxane with a suitable amount of an acidic hydrogen free organic borane compound selected from those having the formulas

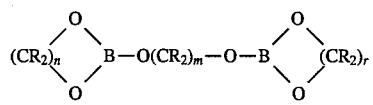

and

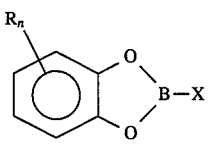

and

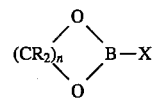

and

and

-continued

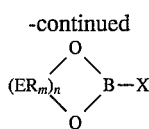

and R₂BOBR₂ wherein each R is individually selected from hydrogen and hydrocarbyl radicals, preferably aryl or alkyl radicals having 1 to 20 carbon atoms; n, m, and r are integers preferably in the range of 1 to 10; each E is individually selected from C, Si, Ge, Sn, B, Ga, In, P, As with the provisio that at least one E is not C, and Sb; and X is selected from hydrogen, hydrocarbyl radicals having 1 to 20 carbon atoms, halides, hydrocarbyloxy radicals having 1 to 20 carbon atoms, and —NR₂ radicals.

6. A process according to claim 5 wherein said polymerization is conducted under particle form conditions.

7. A process according to claim 6 which is conducted in a continuous loop reactor.

8. A process according to claim 7 wherein said solid alkylaluminoxy product is produced by reacting catechol borane with an alkylaluminoxane.

9. A process according to claim 8 wherein said olefin polymerization catalyst comprises a metallocene.

10. A process according to claim 9 wherein said solid alkylaluminoxy product is prepared by reacting catechol borane with methylaluminoxane and said polymerization catalyst comprises at least one metallocene selected from the group consisting of bis(n-butyl cyclopentadienyl) zirconium dichloride and bis(cyclopentadienyl) zirconium dichloride.

11. A process according to claim 10 wherein said olefin consists essentially of ethylene, and said polymerization is conducted in the presence of hydrogen.

12. A process according to claim 5 wherein said solid organo-aluminoxy product is prepared by contacting said borine compound with a solution comprising a hydrocarbyl aluminoxane and a trialkylaluminum.

13. A process according to claim 12 wherein said hydrocarbyl aluminoxane accounts for at least about 50 mole percent of the total aluminum in the solution that is contacted with the borane compound.

14. A process according to claim 13 wherein said trialkylaluminum accounts for no more than about 35 mole percent of the aluminum in the solution that is contacted with the borane compound.

15. A process according to claim 14 wherein said hydrocarbyl aluminoxane in said solution contains at least one unit of the formula

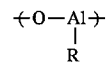

wherein R is an alkyl radical having 1 to 8 carbon atoms.

16. A process according to claim 15 wherein said hydrocarbyl aluminoxane in said solution consists essentially of methylaluminoxane.

17. A process according to claim 16 wherein said trialkylaluminum in said solution consists essentially of trimethylaluminum.

18. A process according to claim 17 wherein the borane compound consists essentially of catechol borane.

19. A process according to claim 18 wherein a solution comprising methylaluminoxane and trimethylaluminum is contacted with a countersolvent for the methylaluminoxane to result in a slurry containing solid methylaluminoxane and then said slurry is contacted with the borane compound to produce the solid aluminoxy product.

20. A process according to claim 19 wherein a particulate diluent is present when said borane compound is contacted with said slurry of aluminoxane.

21. A process according to claim 19 wherein said borane compound is employed in an amount such that the atomic ratio of the boron in the borane compound to the calculated alumina of the aluminoxy units in the aluminoxane is in the range of from about 1:20 to about 1:3.

22. A process according to claim 21 wherein an aliphatic liquid solution of the borane compound is added to said slurry of said methylaluminoxane and trialkylaluminum.

23. A process according to claim 22 wherein a particulate diluent is present when the borane compound is contacted with said methylaluminoxane and trimethylaluminum.

24. A process according to claim 5 wherein said borane compound consists essentially of catechol borane.

25. A process according to claim 24 wherein the catechol borane is employed in an amount such that the atomic ratio of the boron in the borane compound to the calculated aluminum in the aluminoxy units of the aluminoxane is in the range of about 1:20 to about 1:3.

26. A process according to claim 25 wherein a solution comprising methylaluminoxane and trimethylaluminum is contacted with a countersolvent to result in a slurry containing solid methylaluminoxane and then said slurry is contacted with the catechol borane to produce said final solid aluminoxy product.

* * * * *

UNITED STATES PATENT AND TRADEMARK OFFICE
CERTIFICATE OF CORRECTION

PATENT NO. : 5,480,848
DATED : January 2, 1996
INVENTOR(S) : Rolf L. Geerts

It is certified that error appears in the above-indentified patent and that said Letters Patent is hereby corrected as shown below:

Column 11, line 3, claim 12, "borine" should be --borane --.

Signed and Sealed this

Fifth Day of March, 1996

Attest:

BRUCE LEHMAN

Attesting Officer    Commissioner of Patents and Trademarks